US006709413B1

United States Patent
Chance et al.

(10) Patent No.: US 6,709,413 B1
(45) Date of Patent: Mar. 23, 2004

(54) PLATELET GEL MANUFACTURER FOR USE IN A CLOSED CORPOREAL CIRCUIT

(75) Inventors: Nancy Chance, Noblesville, IN (US); Rochelle Strong, Noblesville, IN (US)

(73) Assignee: Riverview Hospital, Noblesville, IN (US)

( * ) Notice: Subject to any disclaimer, the term of this patent is extended or adjusted under 35 U.S.C. 154(b) by 239 days.

(21) Appl. No.: 09/654,020

(22) Filed: Sep. 1, 2000

Related U.S. Application Data (60) Provisional application No. 60/152,034, filed on Sep. 2, 1999.

(51) Int. Cl.[7] .......................... A61M 37/00; C02F 1/38; A61K 35/16
(52) U.S. Cl. .................... 604/6.04; 604/4.01; 210/782; 424/530
(58) Field of Search .................. 604/4.01, 5.01, 604/6.01, 6.04, 6.09, 6.11, 6.157, 82–92; 424/93.72; 210/781, 782, 645; 606/213–215

(56) References Cited

U.S. PATENT DOCUMENTS

| | | | | |
|---|---|---|---|---|
| 5,674,394 A | * | 10/1997 | Whitmore | 210/321.8 |
| 5,733,545 A | * | 3/1998 | Hood, III | 424/529 |
| 5,788,662 A | * | 8/1998 | Antanavich et al. | 210/782 |
| 6,001,259 A | * | 12/1999 | Whitmore | 210/651 |
| 6,197,194 B1 | * | 3/2001 | Whitmore | 210/321.8 |
| 6,200,287 B1 | * | 3/2001 | Keller et al. | 210/767 |
| 6,444,228 B1 | * | 9/2002 | Baugh et al. | 424/529 |
| 2001/0055621 A1 | * | 12/2001 | Baugh et al. | 424/530 |
| 2002/0022213 A1 | * | 2/2002 | Dolecek et al. | 435/2 |

* cited by examiner

*Primary Examiner*—Angela D. Sykes
*Assistant Examiner*—Leslie Deak
(74) *Attorney, Agent, or Firm*—E. Victor Indiano; Indiano, Vaughn, Rebats & Filomena (57) ABSTRACT

The platelet gel manufacturer includes a platelet gel applicator, a controllable platelet receptacle, a controllable coagulant receptacle, and a controllable platelet gel receptacle. The controllable platelet receptacle is fluidly coupled to the closed corporeal system, the controllable coagulant receptacle is fluidly coupled to the controllable platelet gel receptacle, and the controllable platelet gel receptacle is fluidly coupled to the platelet gel applicator. The controllable platelet receptacle is operable to receive the platelet rich plasma obtained from the patient by the closed corporeal system, and controllably deliver the platelet rich plasma to the controllable platelet gel receptacle. The controllable coagulant receptacle is operable to store a coagulant used to produce platelet gel, and controllably deliver the coagulant to the controllable platelet gel receptacle. The controllable platelet gel receptacle is operable to receive the platelet rich plasma from the controllable platelet receptacle, receive the coagulant from the controllable coagulant receptacle, and controllably deliver a platelet gel comprising the platelet rich plasma and the coagulant to the platelet gel applicator. Further, the platelet gel applicator is operable to receive platelet gel from the controllable platelet gel receptacle, and deliver the platelet gel to a selected location of the patient in order to promote healing at the selected location.

19 Claims, 2 Drawing Sheets

PLATELET GEL MANUFACTURER FOR USE IN A CLOSED CORPOREAL CIRCUIT

REFERENCE TO OTHER APPLICATIONS

This application claims the benefit of U.S. Provisional Application No. 60/152,034, filed Sep. 2, 1999, the disclosure of which is hereby incorporated by reference.

TECHNICAL FIELD OF THE INVENTION

The present invention relates to a blood circulating medical device, and more particularly to a device for preparing a blood platelet gel in a closed circuit system wherein the closed circuit system utilizes only the blood of the patient being operated on, for infusing blood and platelet gel into the patient.

BACKGROUND OF THE INVENTION

In certain surgical procedures it is common for blood to be given to the patient during the procedure. In most cases, this blood is supplied through a transfusion wherein the blood being given to the patient is blood that is provided by a third party, or is supplied by the patient herself from blood the patient donated earlier to a blood bank for use in the surgery.

However, such blood transfusions are not suitable for all patients. For example, patients of certain religious groups (e.g. Jehovah's Witness) cannot accept blood transfusions because it violates their religious beliefs. This prohibition usually extends not only to blood transfusions from third parties, but also blood transfusions that originated from the patient herself from earlier withdrawn blood. For example, it would be a violation of certain religious beliefs to withdraw a pint of blood (commonly known as a unit) from the patient prior to surgery, and then reintroduce the blood into the same patient at a later date.

In order to comply with these religious requirements, blood can be withdrawn from the patient, so long as the blood is placed into a closed loop, unbroken circuit, and then reintroduced into the patient from that circuit, without the circuit being broken.

Another issue in blood transfusion operations relates to the issue of stanching the flow of blood from the arteries and/or veins that are cut during surgery. During the middle ages and thereafter, it was common practice during a medical operation, such as a leg amputation, to cut off the flow from blood vessels by placing a hot poker against the open ends of the blood vessels to seal the blood vessels shut through melting the blood vessels together. This process was extremely painful, and was known commonly as cauterization. Although cauterization of the type practiced during the middle ages is no longer performed, some cauterization techniques are still used in certain circumstances.

An advancement over cauterization involves the use of physically closing the arteries with a non-heated object, such as by using a needle and thread to sew the artery or vein shut, thereby preventing blood from flowing out of the artery or vein. Another technique exists that involves the use of a "glue" that comprises a mixture of fiber and glue. The fiber and glue is used in some procedures to actually glue the ends of the arteries or veins shut, hereby stanching the flow of blood.

In recent years, an improved "platelet gel" method has been invented for stanching the flow of blood. The original platelet gel technology was developed at the United States Naval Hospital in San Diego, Calif. by Dr. Paul S. Potter and Mr Andrew G. Hood. Dr. Potter and Mr. Hood discovered that the platelet gel, when applied to a wound, would stop tie flow of bleeding.

Platelet gel technology uses the clotting factors found in the blood's platelets to cause clots within the arteries or veins, thereby stanching the flow of blood from the blood vessels. The platelet gel technique basically involves the manufacture of a platelet gel from platelets harvested from blood. The harvested platelets are mixed with various materials to form a gel, and the gel is applied to the wound. Platelet gel technology is currently used rather extensively in cardiovascular surgeries, orthopaedic surgeries, and in ear, nose and throat surgeries.

The harvesting of platelet cells from blood usually requires that whole blood be separated into fractions through centrifigation. During the centrifugation of blood, the blood separates into three fractions. In particular, the red cell fraction comprising mostly red blood cells migrates to the radially outer portion of the centrifuge tube or barrel, and the plasma fraction migrates to the radially inner portion of the centrifuge tube or barrel since the plasma fraction is half as dense as the red cell fraction. The centrifugation of blood causes a platelet rich fraction to form at a position radially outward of the plasma fraction, and radially inward of the red cell fraction. Basically, the platelet rich fraction between the red cell fraction and the plasma fraction includes platelets in a bed of white cells (i.e. leukocytes). As is well known, white blood cells help fight infection in a wound. More specifically, the platelet rich fraction includes white cells, a few red cells, a small amount of plasma, and a high quantity of platelets. The platelet rich fraction is commonly referred to as platelet rich plasma (PRP).

Each platelet has three growth hormones per platelet. For instance, a sample of blood having a 1,000,000 platelet count would also have a 3,000,000 growth hormone count. When the platelet gel is placed into the wound, the growth hormones of the platelets tend to accelerate the healing process within the wound. Also, the white cells are activated by being placed into the wound and begin to fight infection. Because the wound has been open, the white blood cells in the platelet gel become a defense mechanism within the wound.

The existence of these white cells within the platelet gel make the platelet gel superior to the "artificial glue" discussed above, since the artificial glue has neither the growth hormones nor white blood cells (i.e. leukocytes). As such the artificial glue does not accelerate the healing process and does not furnish the wound with a natural defense mechanism that defends the wound against infection.

While the above described platelet gel technology has many benefits to current surgical procedures, known platelet gel techniques suffer some deficiencies. In particular, no known technique has the capability of being used in a closed corporeal circuit. Further, prior known techniques do not lend themselves to use with a closed corporeal circuit.

As discussed above, a closed corporeal circuit is a circuit wherein blood is drawn from the body, such as by being suctioned out of an open wound, passed through a flow path within a network of tubing, centrifuged in a cell washer (e.g. a Fresenius CATS device), and then returned to the body without ever leaving the circuit. Normally, a circuit such as that described above is unnecessary. However, for those who refuse transfusions, the use of such a circuit is the only viable way that lost blood can be restored.

One problem with the refusal to accept a transfusion is that such a refusal increases the risk faced by the patient during surgery because of the inability to supply the patient with additional blood. Due to the increased risk and possibly enhanced malpractice liability, many surgeons and doctors refuse to perform surgery on such patients. Therefore, a refusal to accept transfusions also limits the availability of practitioners who are willing to perform surgery on the patient.

An additional way that the use of a platelet gel helps to reduce the risk of surgery is that the platelet gel helps the surgeon identify "bleeders," which are blood vessels which have been cut or nicked, and are therefore leaking blood. When the platelet gel is placed into the wound, the bleeders actually pulsate against the platelet gel, thus providing an additional visual indication of the bleeder. If the identified bleeder is large, the surgeon may clear the platelet gel from the bleeder, cauterize the bleeder, and then re-apply the platelet gel before closing the patient. By identifying the bleeders in the above manner, the physician and the patient are spared the trauma of going back into surgery to stop a previously unidentified bleeder.

SUMMARY OF THE INVENTION

The present invention addresses the above-identified need, as well as others, with a platelet gel manufacturer for use with a closed corporeal system that is operable to intravenously extract blood from a patient and separate extracted blood to obtain platelet rich plasma. The platelet gel manufacturer includes a platelet gel applicator, a controllable platelet receptacle, a controllable coagulant receptacle, and a controllable platelet gel receptacle. The controllable platelet receptacle is fluidly coupled to the closed corporeal system, the controllable coagulant receptacle is fluidly coupled to the controllable platelet gel receptacle, and the controllable platelet gel receptacle is fluidly coupled to the platelet gel applicator. The controllable platelet receptacle is operable to receive the platelet rich plasma obtained from the patient by the closed corporeal system, and controllably deliver the platelet rich plasma to the controllable platelet gel receptacle. The controllable coagulant receptacle is operable to store a coagulant used to produce platelet gel, and controllably deliver the coagulant to the controllable platelet gel receptacle. The controllable platelet gel receptacle is operable to receive the platelet rich plasma from the controllable platelet receptacle, receive the coagulant from the controllable coagulant receptacle, and controllably deliver a platelet gel comprising the platelet rich plasma and the coagulant to the platelet gel applicator. Further, the platelet gel applicator is operable to receive platelet gel from the controllable platelet gel receptacle, and deliver the platelet gel to a selected location of the patient in order to promote healing at the selected location.

Pursuant to another embodiment of the present invention, there is provided a system suitable for manufacturing and delivering platelet gel in a closed corporeal circuit. The system includes a blood draw system, a blood pheresis system, and a platelet gel manufacturer. The blood draw system includes a blood reservoir operable to store blood, and an intravenous draw tube operable to draw blood from a vein of a patient and deliver the blood to the blood reservoir. The blood pheresis system includes a centrifuge fluidly coupled to the blood reservoir in order to receive the blood from the blood reservoir. The centrifuge extracts platelet rich plasma comprising platelets and white blood cells from the blood of the patient. The platelet gel manufacturer is fluidly coupled to the blood pheresis system in order to receive the platelet rich plasma. The platelet gel manufacturer is operable to combine the platelet rich plasma with a coagulant to obtain a platelet gel, and deliver the platelet gel to a selected location of the patient in order to promote healing at the selected location.

Pursuant to a further embodiment of the present invention, a platelet gel manufacturer for use with a closed corporeal system is operable to intravenously extract blood from a patient and separate extracted blood to obtain platelet rich plasma. The platelet gel manufacturer includes a platelet gel applicator, a first platelet syringe, a coagulant syringe, a first platelet gel syringe, and tubing. The tubing fluidly couples the platelet gel applicator, the first platelet syringe, the coagulant syringe, and the first platelet gel syringe. The first platelet syringe is operable to receive a first portion of the platelet rich plasma obtained from the patient by the closed corporeal system, and controllably deliver the first portion of the platelet rich plasma to the first platelet gel syringe via the tubing. The coagulant syringe stores a coagulant used to produce platelet gel, and delivers a first portion of the coagulant to the first platelet gel syringe via the tubing. The first platelet gel syringe receives the platelet rich plasma from the first platelet syringe via the tubing, receives the coagulant from the coagulant syringe via the tubing, and controllably delivers a first platelet gel comprising the first portion of the platelet rich plasma and the first portion of the coagulant to the platelet gel applicator via the tubing. The platelet gel applicator receives platelet gel from the first platelet gel syringe, and delivers the platelet gel to selected locations of the patient in order to promote healing at the selected locations.

It is an object of the present invention to provide an improved platelet gel manufacturer and system for manufacturing platelet gel.

It is also an object of the present invention to provide a new and useful platelet gel manufacturer and system for manufacturing platelet gel.

It is another object of the present invention to provide a system of manufacturing platelet gel in a closed corporeal circuit.

It is yet another object of the present invention to provide a platelet gel manufacturer suitable for manufacturing and delivering platelet gel to patients whose religious beliefs do not permit blood transfusions such Jehovah's Witnesses.

The above and other objects, features, and advantages of the present invention will become apparent from the following description and the attached drawings.

DETAILED DESCRIPTION OF EXEMPLARY EMBODIMENTS

While the invention is susceptible to various modifications and alternative forms, exemplary embodiments thereof have been shown by way of example in the drawings and will herein be described in detail. It should be understood, however, that there is no intention to limit the invention to the particular forms disclosed. Rather, the intention is to cover all modifications, equivalents, and alternatives falling within the spirit and scope of the invention as defined by the appended claims.

The Apparatus

Figure 1:
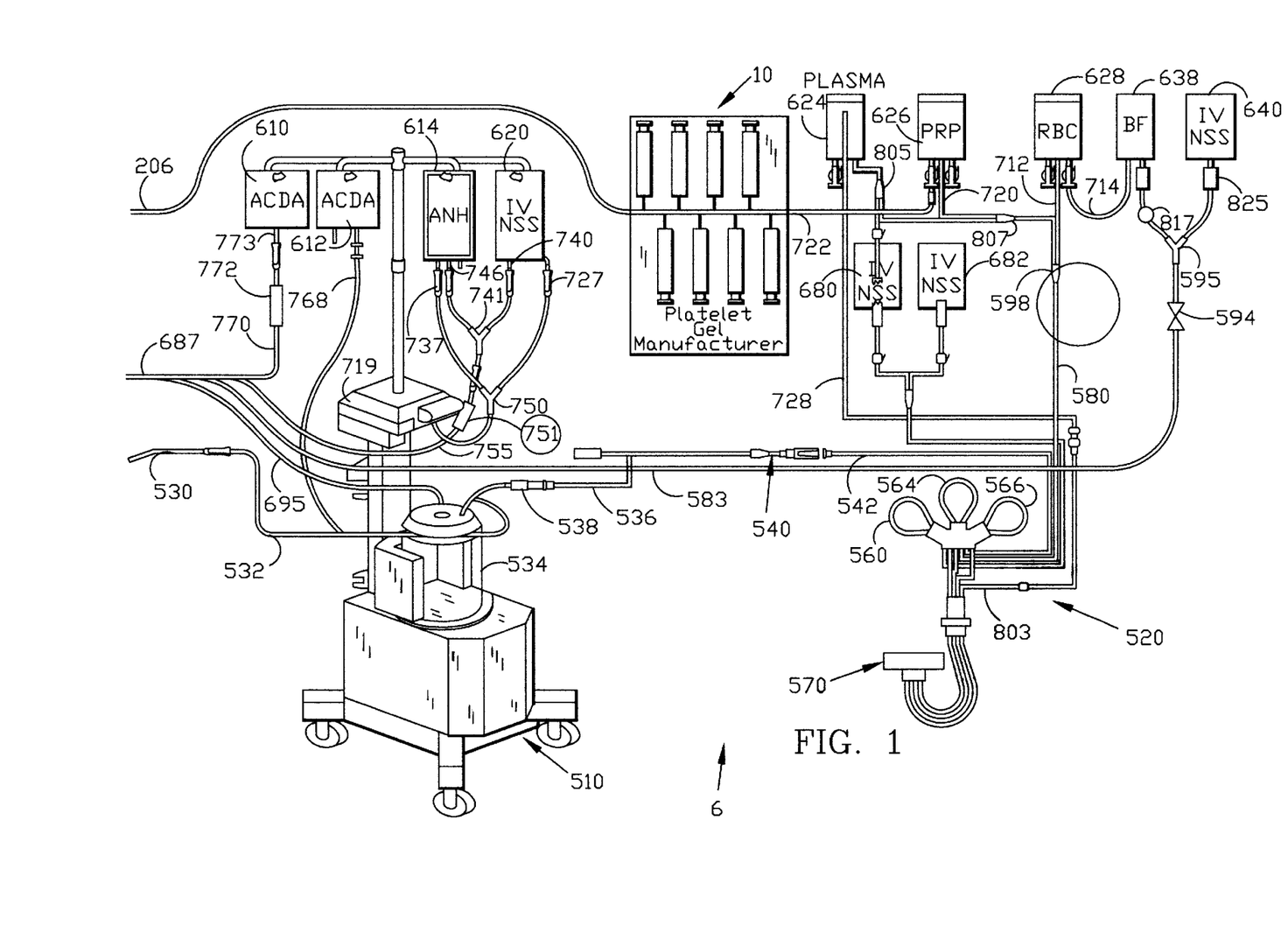
FIG. 1 is a schematic view of a closed corporeal blood circuit system of the present invention.

Turning now to FIG. 1, a closed corporeal platelet gel system 6 incorporating various features of the present invention is shown. The closed corporeal platelet gel system 6 includes a platelet gel manufacturer 10, a blood draw system 510, and a blood pheresis system 520. In an exemplary embodiment, the blood draw system 510 includes a Quick-Draw blood draw system manufactured by Harvest Technologies in addition to other components, and the blood pheresis system 520 includes a C.A.T.S (Continuous AutoTransfusion System) manufactured by Fresenius Hemotechnology, Inc. in addition to other components. While the exemplary closed corporeal platelet gel system 6 includes a Harvest QuickDraw blood draw system and a Fresenius C.A.T.S, the closed corporeal platelet gel system 6 may alternatively be implemented with blood draw systems and blood pheresis systems made by other manufacturers. Further, while the exemplary closed corporeal platelet gel system 6 is generally implemented with off-the-shelf components, the closed corporeal platelet gel system 6 may alternatively be implemented as an integrated system specifically designed for closed corporeal platelet gel manufacturing.

As depicted, blood draw system 510 includes a suction tube 530 and a reservoir 534. The suction tube 530 is fluidly coupled to, and upstream of an introduction tube 532 which itself is fluidly coupled to, and upstream of a reservoir 534. Under the influence of a vacuum, the suction tube 530 is operable to salvage blood from a wound of a patient and transfer the salvaged blood to the reservoir 534. The reservoir 534 of the exemplary embodiment is a generally coffee can shaped jug or jar that includes a filter (not shown) located toward the bottom of the reservoir 534. The bottom filter of the reservoir 534 filters blood as the blood is drawn through the bottom filter and transferred to the blood pheresis system 520 or the ANH bag 614.

In an exemplary embodiment, fluid communication between the blood draw system 510 and the blood pheresis system 520 is accomplished via a wedding valve 538, a spike tube 536, and an adaptator 540 of a disposable pheresing kit available from the Fresenius Hemotechnology, Inc. which configures the C.A.T.S device for blood pheresing. In particular, the wedding valve 538, the spike tube 536, and the adaptator 540 fluidly couple the reservoir 534 of the blood draw system 510 to the centrifuge 570 of the blood pheresing system 520, so that blood may be transported from the blood draw system 510 to the centrifuge 570 of the blood pheresis system 520.

Fluid communication between the blood draw system 510 and the blood pheresis system 520 may alternatively be implemented with a straight, device-free tubing instead of the wedding valve 538, the spike 536 and the adaptation 540. The advantage of using the wedding valve 538, the spike 536 and the adaptation 540 is that fluid communication is accomplished by using only off-the-shelf components. The use of straight, device-free tubing between the blood draw system 510 and the blood pheresis system 520 is operable, but has the disadvantage of requiring specifically fabricated parts, as opposed to the primary off-the-shelf components used to construct the exemplary closed corporeal platelet gel system 6.

The blood draw system 510 further includes an anticoagulant bags 610, 612, an Acute Normovolumetric Hemodilution (ANE) bag 614, an intravenous normal saline solution (IV NSS) bag 620, and a blood draw/infusion tube 687. In an exemplary embodiment, the blood draw/infusion tube 687 is fluidly coupled to the reservoir 534 via blood draw tube 695 and includes a catheter (not shown) for making a closed intravenous connection with a patient. For example, the blood draw/infusion tube 687 may be implemented with a catheter suitable for making an intravenous connection at (i) the patient's antecubital region (i.e. the anterior part of the elbow where blood is most commonly drawn) or (ii) the patient's jugular region.

The anticoagulant bag 610 is generally used to store an anticoagulant such as a citrate dextrose anticoagulant (ACDA) used to maintain fluid/blood flow through blood draw/infusion tube 687. To this end, the anticoagulant bag 610 is coupled to the blood draw/infusion tube 687 via a switch 773, a measuring device 772, and a tube 770. In an exemplary embodiment, the measuring device 772 is implemented with a buritrol. A BURITROL is basically a restrictive device for delivering an exact amount of fluid and therefore helps prevent the entire bag of anticoagulant from infusing back into the blood draw/infusion tube 687 with a "one-time" short burst. The switch 773 is positioned between the anticoagulant bag 610 and the measuring device 772. The switch 773 in the exemplary embodiment is implemented with a valve clamp that controls the amount of anticoagulant flow from the anticoagulant bag 610 to the measuring device 772. Accordingly, the measuring device 772 and the switch 773 provide a mechanism for controlling the anticoagulant rate of flow from the anticoagulant bag 610 to the blood draw/infusion tube 687.

Due to the above interconnection of anticoagulant bag 610 and blood draw/infusion tube 687, anticoagulant flows from anticoagulant bag 610 through switch 773, measuring device 772, and tube 770 into blood draw/infusion tube 687. From the blood draw/infusion tube 687, the anticoagulant flows to the reservoir 534 via the blood draw tube 695. In this manner, the anticoagulant of anticoagulant bag 610 helps prevent blood and other blood components from coagulating in the blood draw/infusion tube 687.

The anticoagulant bag 612 is generally used to store an anticoagulant such as a citrate dextrose anticoagulant (ACDA) that is used to maintain fluid/blood flow through suction tube 530. To this end, the anticoagulant bag 612 is fluidly coupled to the suction tube 530 via tube 768. As a result of being fluidly coupled to the suction tube 530, anticoagulant flows from bag 612 through the suction tube 530 and into the reservoir 534 during operation.

The ANH bag 614 is generally used to store an Acute Normovolumetric Hemodilution (ANH) which is essentially whole blood drawn from the patient just prior to surgery (i.e. just prior to making an incision). To this end, the ANH bag 614 is fluidly coupled to the reservoir 534 via valve 737 and Y-connector 750 in order to receive blood drawn from the patient. In order to return the drawn ANH back to the patient, the ANH bag 614 is further fluidly coupled to the blood draw/infusion tube 687. More specifically, the ANH bag 614 is coupled to the blood draw/infusion tube 687 via valve 746, Y-connector 741, and a SQ-40 filter 751.

The SQ-40 filter 751 is further coupled to an Abbot return path blood filter 755 that is coupled to the blood draw/infusion tube 687.

The IV NSS bag 620 is generally used to store normal saline solution which is used to help keep the Abbott return path 755 continuously open. To this end, the IV NSS bag 620 is fluidly coupled to the Abbott return path 755 via valve 740, Y-connector 741, the SQ-40 filter 751. The SQ-40 filter 751 is further coupled to an Abbot return path blood filter 755 that is coupled to the blood draw/infusion tube 687. Furthermore, the IV NSS bag 620 is fluidly coupled to the reservoir 534 via valve 727 and Y-connector 750.

Referring now to the blood pheresis system 520 of the closed corporeal platelet gel system 6, the blood pheresis system 520 generally includes a cell wash pump 560, a centrifuge output pump 564, a blood pump 566, and a centrifuge 570 which are generally operable to separate blood into its constituent components. Moreover, the blood pheresis system 520 includes various bags operable to store blood components and fluids used by the closed corporeal platelet gel system 6. In particular, the blood pheresis system 520 includes a plasma bag 624, a platelet rich plasma (PRP) bag 626, a red blood cell (RBC) bag 628, a blood filter (BF) bag 638, and three IV bags 640, 680, 682.

The centrifuge 570 is generally operable to separate blood into its constituent components. To this end, the centrifuge essentially includes a compartment that is spun about a central axis in order to separate materials of different specific gravities. In particular, as a result of spinning blood about the central axis, the centrifuge 570 separates the blood into at least a plasma fraction, a platelet rich plasma fraction, a red blood cell fraction.

The plasma bag 624 is generally operable to store the plasma fraction obtained by the centrifuge 570 until the plasma fraction is later infused into the patient. To this end, the plasma bag 624 is fluidly coupled to the centrifuge 570 via centrifuge output tube 580 and centrifuge output pump 564 in order to receive the plasma fraction obtained by the centrifuge 570. More specifically, the plasma bag 624 is fluidly coupled to the centrifuge 570 via bifurcations 805, 807, and 598. The plasma bag 624 is also fluidly coupled to the centrifuge 570 via centrifuge input tube 803 in order to deliver the plasma to the centrifuge 570 in route to being infused into the patient. Moreover, the plasma bag 624 is fluidly coupled to the centrifuge 570 via cell wash pump 560 which controls the flow of fluid into the centrifuge 570 during cell washing.

The platelet rich plasma (PRP) bag 626 is generally operable to store the platelet rich plasma fraction obtained by the centrifuge 570. Specifically, in an exemplary embodiment, the PRP bag 626 is operable to hold at least 101 cubic centimeters of the platelet rich plasma fraction. To this end, the PRP bag 626 is fluidly coupled to the centrifuge output tube 580 and the centrifuge output pump 564 via bifurcation 807 and 598 in order to receive the platelet rich plasma fraction obtained by the centrifuge 570. The PRP bag 626 is further fluidly coupled to the platelet gel manufacturer 10 in order to supply the platelet gel manufacturer 10 with platelet rich plasma from which to manufacturer platelet gel.

The red blood cell (RBC) bag 628 is generally operable to store the red blood cell fraction obtained by the centrifuge 570. To this end, the RBC bag 628 is fluidly coupled to the centrifuge output tube 580 and the centrifuge output pump 564 via bifurcation 598 in order to receive the red blood cell fraction obtained by the centrifuge 570. The RBC bag 628 is further fluidly coupled to the blood filter bag 630.

The blood filter bag 638 is generally operable to store and filter blood fractions prior to infusing the blood fractions into the patient. To this end, the blood filter bag 638 is fluidly coupled to the blood draw/infusion tube 687 via a Pall Filter 817 (e.g. Purcell, SQ40), Y-connector 595, valve 594, tube 583, and the blood draw/infusion tube 687.

Furthermore, the IV NSS bags 640, 680, 682 of the blood pheresis system 520 are generally operable to store intravenous saline solution. In particular, IV NSS bags 680, 682 are generally used to wash the blood cells in the centrifuge 570 during the pheresis process. To this end, the IV NSS bags 680, 682 are fluidly coupled to the centrifuge 570 via cell wash pump 560 which controls the flow of fluid into the centrifuge 570 during cell washing. The IV NSS bag 640 on the other hand is generally used to keep tube 583 and the blood draw/infusion tube 687 open. To this end, the IV NSS bag 640 is coupled to the blood draw/infusion tube 687 via a valve 825, the Y-connector 595, valve 594, and tube 583.

The three pumps 560, 564, a lid 566 of the blood pheresis system 520 generally represent three independent fluid flow paths wherein the fluid of the cell wash pump 560 is not intermingled with the fluid of the centrifuge output pump 564 or the blood pump 566. Each of the three pumps 560, 564 and 566 includes a three-in-one switch that enables independently controlled operation of the three pumps 560, 564 and 566.

The cell wash pump 560 generally controls the flow of normal intravenous saline solution from IV bags 680, 682 to the centrifuge 570 during the pheresis process. The centrifuge output pump 564 generally controls the flow of the separable blood fractions from the centrifuge 570 to the corresponding plasma bag 624, the platelet rich plasma bag 626, and the red blood cell bag 628. The blood pump 566 generally controls the flow of blood from the reservoir 534 of the blood draw system 510 to the centrifuge 570 of the blood pheresis system 520.

Figure 2:
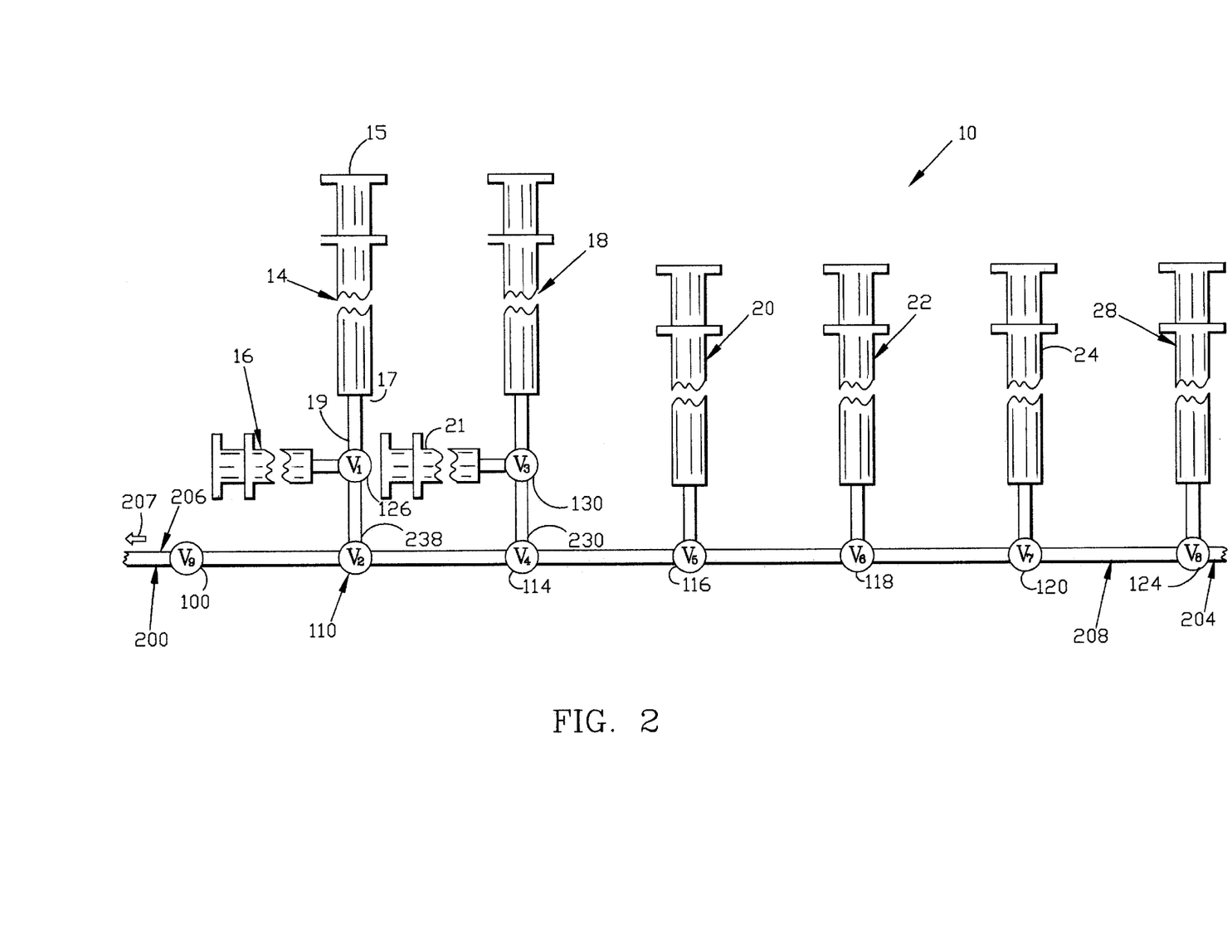
FIG. 2 is a schematic view of the platelet gel manufacturer of the present invention.

The platelet gel manufacturer 10 of the closed corporeal platelet gel system 6 is depicted in detail in FIG. 2. In general, the platelet gel manufacturer 10 is operable to receive platelet rich plasma from the blood pheresis system 520, manufacture platelet gel from the received platelet rich plasma, and controllably apply the platelet gel to a patient in order to coupled to the blood draw/infusion tube 687. Furthermore, the IV NSS bag 620 is fluidly coupled to the reservoir 534 via valve 727 and Y-connector 750.

Referring now to the blood pheresis system 520 of the closed corporeal platelet gel system 6, the blood pheresis system 520 generally includes a cell wash pump 560, a centrifuge output pump 564, a blood pump 566, and a centrifuge 570 which are generally operable to separate blood into its constituent components. Moreover, the blood pheresis system 520 includes various bags operable to store blood components and fluids used by the closed corporeal platelet gel system 6. In particular, the blood pheresis system 520 includes a plasma bag 624, a platelet rich plasma (PRP) bag 626, a red blood cell (RBC) bag 628, a blood filter (BF) bag 638, and three IV bags 640, 680, 682.

The centrifuge 570 is generally operable to separate blood into its constituent components. To this end, the centrifuge essentially includes a compartment that is spun about a central axis in order to separate materials of different specific gravities. In particular, as a result of spinning blood about the central axis, the centrifuge 570 separates the blood into at least a plasma fraction, a platelet rich plasma fraction, a red blood cell fraction.

The plasma bag 624 is generally operable to store the plasma fraction obtained by the centrifuge 570 until the plasma fraction is later infused into the patient. To this end, the plasma bag, 624 is fluidly coupled to the centrifuge 570 via centrifuge output tube 580 and centrifuge output pump 564 in order to receive the plasma fraction obtained by the centrifuge 570. More specifically, the plasma bag 624 is fluidly coupled to the centrifuge 570 via bifurcations 805, 807, and 598. The plasma bag 624 is also fluidly coupled to the centrifuge 570 via centrifuge input tube 803 in order to deliver the plasma to the centrifuge 570 in route to being infused into the patient. Moreover, the plasma bag 624 is fluidly coupled to the centrifuge 570 via cell wash pump 560 which controls the flow of fluid into the centrifuge 570 during cell washing.

The platelet rich plasma (PRP) bag 626 is generally operable to store the platelet rich plasma fraction obtained by the centrifuge 570. Specifically, in an exemplary embodiment, the PRP bag 626 is operable to hold at least 101 cubic centimeters of the platelet rich plasma fraction. To this end, the PRP bag 626 is fluidly coupled to the centrifuge output tube 580 and the centrifuge output pump 564 via bifurcation 807 and 598 in order to receive the platelet rich plasma fraction obtained by the centrifuge 570. The PRP bag 626 is further fluidly coupled to the platelet gel manufacturer 10 in order to supply the platelet gel manufacturer 10 with platelet rich plasma from which to manufacturer platelet gel. stop bleeding and promote healing at the point of application. To this end, the platelet gel manufacturer to includes a central flow tube 200, an input tube 204 that fluidly couples the central flow tube 200 to the PRP bag 624, and a platelet gel applicator 206 that is fluidly coupled to the central flow tube 200. The platelet gel applicator 206 in the exemplary embodiment is at least 24 inches long and flexible to provide sufficient range and mobility for applying the platelet gel into a wound of the patient. Fluid generally flows through the platelet gel manufacturer 10 in the direction denoted by arrow 207.

The platelet gel manufacturer 10 further includes valves 100, 110, 114, 116, 118, 120, 124, 126, 130 and controllable receptacles 14, 16, 18, 20, 22, 24, 28. In an exemplary embodiment, the valves 100, 110, 114, 116, 118, 120, 124, 126, 130 are implemented with manually operated stopcock type valves that enable the operator to control the flow of fluid through the tube in which the valve is inserted, and also enables the operator to control the flow through the tube. While the exemplary embodiment utilizes manual valves, the platelet gel manufacturer 10 may alternatively be implemented with automated valves which are electronically or hydraulicly actuated and controlled by a properly programed computer system or micro-controller.

The controllable receptacles 14, 16, 18, 20, 22, 24, 28 are generally operable to receive, store, and deliver fluids in a controllable manner. To this end, the controllable receptacles 14, 16, 18, 20, 22, 24, 28 in an exemplary embodiment are implemented with typical syringes. As illustrated in FIG. 2, the controllable platelet gel receptacle 14 illustrates the components of a typical syringe. In particular, the controllable platelet gel receptacle 14 includes a reservoir body portion 17 comprising a hollow interior operable to slideably receive a plunger member 15 at a first end. A relatively smaller diameter output tube 19 is disposed at a second end of the reservoir body portion 17 that is distal to the first end. Slidably positioning the plunger member 15 within the reservoir controls the amount of fluid received, stored, and delivered by the controllable platelet gel receptacle 14 via the output tube 19.

In an exemplary embodiment, the platelet gel manufacturer 10 includes two controllable platelet gel receptacles 14, 16 coupled to a common first valve 126 which in turn is fluidly coupled to the central flow tube 200 via a first tube 238 and a second valve 110. In addition, the platelet gel manufacturer 10 includes two controllable platelet gel receptacles 18, 21 coupled to a common third valve 130 which in turn is fluidly coupled to the central flow tube 200 via a second tube 230 and fourth valve 114. In particular, the second valve 110 and the fourth valve 114 are positioned with respect to the central flow tube such that the fourth valve 114 is closer to the input tube 204. As explained in more detail below, each of the controllable platelet gel receptacles 14, 16, 18, 21 in the exemplary embodiment are implemented with a separate 10 cc syringe that is initially empty and that eventually stores and controllably delivers manufactured platelet gel to the platelet gel applicator 206 of the platelet gel manufacturer 10.

The platelet gel manufacturer 10, in the exemplary embodiment, further includes a controllable coagulant receptacle 20 implemented with a 20 cc syringe containing 10 percent calcified thrombin (a clotting agent) (5000 units) that is coupled to a fifth valve 116. In particular, the fourth valve 114 and the fifth valve 116 are positioned with respect to the central flow tube 200 such that the fifth valve 116 is closer to the input tube 204.

Further yet, the platelet gel manufacturer 10, in the exemplary embodiment, includes two controllable platelet receptacles 22, 24 that are respectively coupled to a sixth valve 118 and a seventh valve 120. In particular, the fifth valve 116 and the sixth valve 118 are positioned with respect to the central flow tube 200 such that the sixth valve 118 is closer to the input tube 204, and the sixth valve 118 and the seventh valve 120 are positioned with respect to the central flow tube 200 such that the seventh valve 120 is closer to the input tube 204. As explained in more detail below, each of the controllable receptacles 22, 24 in the exemplary embodiment are implemented with a separate 60 cc syringe that is initially empty; however, the first controllable platelet receptacle 22 eventually receives, stores and controllably delivers 40 cc from a first platelet rich plasma draw, and the second controllable platelet receptacle 24 eventually receives, stores and controllably delivers 60 cc from a second platelet rich plasma draw. The first 40 cc of blood drawn from the patient is the most platelet rich. Accordingly, in operation, the first controllable platelet receptacle 22 receives, stores and controllably delivers a more platelet rich plasma than the second controllable platelet receptacle 24.

The platelet gel manufacturer 10, in the exemplary embodiment, further includes a controllable flushing receptacle 28 implemented with a 60 cc syringe containing normal saline solution that is coupled to an eighth valve 124. In particular, the seventh valve 120 and the eighth valve 124 are positioned with respect to the central flow tube 200 such that the eighth valve 124 is closer to the input tube 204, thus in making the controllable flushing receptacle 28 the closest receptacle to the input tube 204. Accordingly, the controllable flushing receptacle 28 is positioned such that the flushing receptacle 28 can operably flush normal saline solution through the components of the platelet gel manufacturer 10.

Operation of the Device:

As is well known, static blood and platelet rich plasma will coagulate. In order to help prevent the blood and the platelet rich plasma from coagulating, the platelet gel manufacturer 10, the blood draw system 510, and the blood pheresis system 520 are placed on rockers that rock the blood and platelet rich plasma constantly during operation in order to help prevent them from coagulating. Accordingly, the platelet gel manufacturer 10, the blood draw system 510, and the blood pheresis system 520 are designed to withstand constant rocking.

The exemplary procedure begins with an acute normovolumetric hemodilution. To this end, a 16 gauge angiocatheter of the blood draw/infusion tube 687 is placed in the patient's antecubital space (i.e. the elbow area). Anticoagulant in the anticoagulant bag 610 is dripped into the buritrol 772, to deliver 62 cc of anticoagulant to the blood draw system 510. The blood draw system 510 is then turned on in order to vacuum assist the blood draw from the patient. The anticoagulant and the blood drawn from the patient are delivered to the reservoir 534 via the blood draw tube 695. The blood volume collected for the acute normovolumetric hemodilution process is monitored via graduation markings located on reservoir 534.

After a unit of blood has been transferred to the reservoir 534, the blood pump 566 pumps the drawn unit of blood from the reservoir 534 into the centrifuge via the wedding valve 538, the spike tube 536, and the adaptator 540. The centrifuge 570 then spins the drawn blood about a central axis which causes the drawn blood to separate into at least three blood fractions. The centrifuge output pump 564 then pumps the plasma fraction from the centrifuge 570 into the plasma bag 624 via the centrifuge output tube 580 and the bifurcations 598, 807, and 805.

After transferring the plasma to the plasma bag 624, the centrifuge output pump 564 then pumps the red blood cell fraction from the centrifuge 570 into the RBC bag 628 via the centrifuge output tube 580 and the bifurcation 598. The red blood cells collected in the RBC bag 628 are then transferred into the blood filter bag 638 via tube 714. The red blood cells may later be transferred from the blood filter bag 638 and infused into the patient via the Pall filter 817, Y-connector 595, valve 594, tube 583, and the blood draw/infusion tube 687.

After transferring the red blood cells to the RBC bag 628, the centrifuge output pump 564 pumps the first 40 cc of platelet rich plasma into the PRP bag 626 via the centrifuge output tube 580 and the bifurcations 598 and 807. The first 40 cc of the platelet rich plasma is then transferred to the first platelet receptacle 22 of the platelet gel manufacturer 10 via tubes 722, 204 and the sixth valve 118.

After the first 40 cc of platelet rich plasma has been transferred to the first platelet receptacle 22, the centrifuge output pump 564 pumps the next 60 cc of platelet rich plasma into the PRP bag 626 via the centrifuge output tube 580 and the bifurcations 598 and 807. The next 60 cc of the platelet rich plasma is then transferred to the second platelet receptacle 24 of the platelet gel manufacturer 10 via tubes 722, 204 and the seventh valve 120. At that point, the platelet rich plasma continues to rock on the blood bank rocker to which the platelet gel manufacturer 10 is attached, to await the surgeon's decision to utilize it in the patient's wound after surgery is completed.

After obtaining the above blood fractions, approximately two (2) additional units of blood are drawn from the patient and transferred to the reservoir 534. The drawn blood is then transferred to the ANH bag 614 where the ANH blood is stored and rocked by the blood bank rocker. In general, the ANH blood remains in the ANH bag 614 during surgery until the surgeon or anesthesiologist deems that the ANH blood is needed for volume shock or should simply be infused after surgery. In either case, the ANH blood is returned to the patient via valve 746, the Pall filter 751, the Abbot return path 755, and the blood draw/infusion tube 687.

After the acute normovolumetric hemodilution process is completed, a closed corporeal blood salvage is performed. To this end, the suction tube 530 upon incision is placed immediately into the patient. In particular, the surgeon places the suction tube 530 into the wound incision to complete the closed corporeal circuit. As indicated above, the suction tube 530 is fluidly coupled to the reservoir 534 which provides the suction tube 530 with a slight vacuum for salvaging shed blood from the patient. During blood salvage, the anticoagulant bag 612 delivers 30 cc per hour of anticoagulant. The anticoagulant delivered to the blood draw system 510 via the anticoagulant bag 612 and tube 768 both helps to prevent coagulation within the suction tube 530 and the introduction tube 532 and helps to prime the suction tube 530 and the introduction tube 532.

Upon the anesthesiologist's request, the surgeon's request, or at the end of surgery, the blood pump 566 pumps the salvaged blood from the reservoir 534 into the centrifuge 570 via the wedding valve 538, the spike tube 536, and the adaptation 540. In addition, the cell wash pump 560 pumps normal saline solution from either of the IV NSS bags 680, 682 into the centrifuge 570 in order wash the blood cells in the centrifuge 570. The centrifuge 570 then spins the salvaged blood and the normal saline solution about a central axis which causes the salvaged blood to separate into various fractions. The centrifuge output pump 564 then transfers the red blood cell fraction from the centrifuge 570 into the red blood cell bag 628 via the centrifuge output tube 580 and the bifurcation 598. The salvaged red blood cells are typically returned to the patient via the tube 714, the blood filter bag 638, the Pall filter 817, the Y-connector 595, the valve 594, the tube 583, and the blood draw/infusion tube 687.

Besides the suction tube 530, the distal end of the platelet gel applicator 206 is placed into the incision site immediately after the surgeon makes the incision. In general, the distal end of the platelet gel applicator 206 is placed into the patient wound so that the closed corporeal circuit is maintained.

Toward the end of the surgery and prior to closing the incision, there comes a point where the surgeon decides to apply the platelet gel to an incision. As discussed above, the application of a layer of platelet gel to the incision serves to effectively clot the arteries and veins within the incision thus stopping the bleeding in a natural way (i.e. through the clotting of the blood within the arteries and veins). In addition to stopping the bleeding, the platelet gel also promotes healing of the incision.

Once the surgeon is ready to close the wound and asks for platelet gel, the scrub nurse or other utilizes the platelet gel manufacturer 10 to produce platelet gel that the surgeon may apply to the wound. To this end, the scrub nurse first delivers 8 cc of platelet rich plasma to the first controllable platelet gel receptacle 14. In particular, the scrub nurse opens the sixth valve 118 of the platelet gel manufacturer 10 in order to place the first controllable platelet receptacle 22 in fluid communication with the central flow tube 200. In addition, the scrub nurse adjusts the first valve 126 and opens the second valve 110 in order to place the first controllable platelet gel receptacle 14 in fluid communication with the central flow tube 200 and therefore in fluid communication with the first controllable platelet receptacle 22. The scrub nurse then causes the first controllable platelet receptacle 22 to deliver 8 cc of platelet rich plasma to the first controllable platelet gel receptacle 14 via the sixth valve 118, the central flow tube 200, the second valve 110, and the first valve 126. More specifically, the scrub nurse in an exemplary embodiment delivers the 8 cc of platelet rich plasma to the first controllable platelet gel receptacle 14 by pushing the plunger of the syringe used to implement the first controllable platelet receptacle 22.

After delivering the 8 cc of platelet rich plasma, the scrub nurse delivers 1 cc of coagulant to the first controllable platelet gel receptacle 14. To this end, the scrub nurse closes the sixth valve 118 in order to remove the first controllable platelet receptacle 22 from fluid communication with the central flow tube 200. The scrub nurse then opens the fifth valve 116 in order to place the controllable coagulant receptacle 20 in fluid communication with the central flow tube 200 and therefore in fluid communication with the first controllable platelet gel receptacle 14. The scrub nurse then causes the controllable coagulant receptacle 20 to deliver 1 cc of 10 percent calcified thrombin to the first controllable platelet gel receptacle 14 via the fifth valve 116, the central flow tube 200, the second valve 110, and the first valve 126. More specifically, the scrub nurse in an exemplary embodiment delivers the 1 cc of 10 percent calcified thrombin to the first controllable platelet gel receptacle 14 by pushing the plunger of the syringe used to implement the controllable coagulant receptacle 20.

After delivering the 1 cc of coagulant, the scrub nurse places the first controllable platelet gel receptacle 14 in fluid communication with the platelet gel applicator 206 of the platelet gel manufacturer 10. To this end, the scrub nurse adjusts the second valve 110 and the ninth valve 100 such that the first controllable platelet gel receptacle 14 and the platelet gel applicator 206 are in fluid communication with one another.

Once the platelet rich plasma and the coagulant have been transferred to the first controllable platelet gel receptacle 14, the scrub nurse actuates the first controllable platelet gel receptacle 14 to create 1 cc or so of dead space and allows the blood bank rocker to rock the first controllable platelet gel receptacle 14 a few times in order to thoroughly mix the platelet rich plasma with the coagulant. After the platelet rich plasma and the coagulant are thoroughly mixed, the scrub nurse delivers the resulting platelet gel. In particular, the scrub nurse in an exemplary embodiment delivers the platelet gel to the platelet gel applicator 206 by pushing on the plunger 15 of the syringe used to implement the first platelet gel receptacle 14. The surgeon then may use the flexible platelet gel applicator 206 to apply the platelet gel to the incision.

If additional platelet gel is needed, platelet rich plasma and coagulant may be delivered to the second, third, and fourth platelet gel receptacles 16, 18, 21 in a manner similar to above. Moreover, if clotting begins to occur in the platelet gel manufacturer 10, the controllable flushing receptacle 28 at the proximal port of the platelet gel manufacturer 10 could be used to deliver normal saline through the central flow tube 200 and the platelet gel applicator 206 thereby flushing clotting material out of the platelet gel manufacturer 10.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention are desired to be protected.

What is claimed is:

1. A platelet gel manufacturer for use with a closed corporeal system configured for intravenously extracting blood from a patient during a surgical procedure and separating extracted blood to obtain platelet rich plasma, said platelet gel manufacturer comprising a platelet gel applicator, a controllable platelet receptacle, a controllable coagulant receptacle, and a controllable platelet gel receptacle, wherein said controllable platelet receptacle is fluidly coupled to said closed corporeal system, wherein said controllable platelet receptacle is configured to receive said platelet rich plasma obtained from said patient by said closed corporeal system, and controllably deliver said platelet rich plasma to said controllable platelet gel receptacle, said controllable coagulant receptacle is fluidly coupled to said controllable platelet gel receptacle, said controllable coagulant receptacle being configured to store a coagulant used to produce platelet gel, and controllably deliver said coagulant stored therein to said controllable platelet gel receptacle, said controllable platelet gel receptacle is fluidly coupled to said platelet gel applicator, said controllable platelet gel receptacle being configured to receive said platelet rich plasma from said controllable platelet receptacle, receive said coagulant from said controllable coagulant receptacle, and controllably deliver a platelet gel comprising platelet rich plasma and coagulant to said platelet gel applicator, and said platelet gel applicator being configured to receive platelet gel from said controllable platelet gel receptacle, and deliver said platelet gel to a selected location of said patient during the surgical procedure in order to promote healing at said selected location.

2. The platelet gel manufacturer of claim 1, further comprising: tubing that fluidly couples said controllable platelet receptacle, said controllable coagulant receptacle, and said controllable platelet gel receptacle.

3. The platelet gel manufacturer of claim 1, further comprising: tubing that fluidly couples said controllable platelet receptacle, said controllable coagulant receptacle, and said controllable platelet gel receptacle; and a plurality of valves coupled in-line with said tubing, said plurality of valves operable to control flow among said platelet gel applicator, said controllable platelet receptacle, said controllable coagulant receptacle, and said controllable platelet gel receptacle.

4. The platelet gel manufacturer of claim 1, further comprising tubing and a controllable flushing receptacle, wherein said tubing fluidly couples said controllable platelet receptacle, said controllable coagulant receptacle, said controllable platelet gel receptacle, and said controllable flushing receptacle, said controllable flushing receptacle is operable to store intravenous saline, and controllably flush said intravenous saline through said tubing in order to help prevent clotting in said tubing, said platelet rich plasma delivered by said controllable platelet receptacle substantially comprises platelets and white blood cells, and said coagulant delivered by said controllable coagulant receptacle comprises thrombin.

5. The platelet gel manufacturer of claim 1, further comprising tubing and a controllable flushing receptacle, wherein said tubing fluidly couples said controllable platelet receptacle, said controllable coagulant receptacle, said controllable platelet gel receptacle, and said controllable flushing receptacle, said controllable flushing receptacle being configured to store intravenous saline, and controllably flush said intravenous saline through said tubing in order to help prevent clotting in said tubing, said controllable platelet receptacle comprises a first syringe that is configured to receive said platelet rich plasma obtained from said patient by said closed corporeal system, and controllably deliver said platelet rich plasma to said controllable platelet gel receptacle, said controllable coagulant receptacle comprises a second syringe that is configured to store a coagulant used to produce platelet gel, and controllably deliver said coagulant to said controllable platelet gel receptacle, said controllable platelet gel receptacle comprises a third syringe that is configured to receive said platelet rich plasma from said controllable platelet receptacle, receive said coagulant from said controllable coagulant receptacle, and controllably deliver said platelet gel comprising platelet rich plasma and coagulant to said platelet gel applicator, said platelet rich plasma delivered by said first syringe substantially comprising platelets and white blood cells, and said coagulant delivered by said second syringe comprising thrombin.

6. A system for extracting blood from a patient, forming platelet rich plasma from the extracted blood, manufacturing platelet gel from the platelet rich plasma and delivering platelet gel in a closed corporeal circuit back to the patient without the extracted blood, platelet rich plasma or platelet gel being removed from the closed corporeal circuit, the system comprising:

a blood draw system comprising a blood reservoir configured for storing blood, and an intravenous draw tube configured for drawing blood from a vein of a patient and delivering said blood to said blood reservoir;

a blood pheresis system comprising a centrifuge fluidly coupled to said blood reservoir in order to receive said blood from said blood reservoir, wherein the centrifuge is configured for extracting platelet rich plasma comprising platelets and white blood cells from said blood of said patient;

a platelet gel manufacturer fluidly coupled to said blood pheresis system configured for receiving platelet rich plasma from the centrifuge, the platelet gel manufacturer including a platelet gel applicator, wherein said platelet gel manufacturer combines platelet rich plasma with a coagulant to form a platelet gel, and the platelet gel applicator delivers said platelet gel to a selected location of said patient in order to promote healing at said selected location.

7. The system of claim 6, wherein said platelet gel manufacturer further comprises a controllable platelet receptacle, a controllable coagulant receptacle, and a controllable platelet gel receptacle, said controllable platelet receptacle being fluidly coupled to said closed corporeal system, for receiving platelet rich plasma obtained from said patient by said blood pheresis system, and controllably delivering platelet rich plasma to said controllable platelet gel receptacle, said controllable coagulant receptacle being fluidly coupled to said controllable platelet gel receptacle, for storing a coagulant used to produce platelet gel, and controllably delivering coagulant to said controllable platelet gel receptacle, said controllable platelet gel receptacle being fluidly coupled to said platelet gel applicator, for receiving platelet rich plasma from said controllable platelet receptacle, receiving coagulant from said controllable coagulant receptacle, and controllably delivering a platelet gel comprising platelet rich plasma and coagulant to said platelet gel applicator, and said platelet gel applicator receives platelet gel from said controllable platelet gel receptacle, and delivers said platelet gel to a surgical tissue site of said patient.

8. The system of claim 6, wherein said platelet gel manufacturer further comprises a controllable platelet receptacle, a controllable coagulant receptacle, a controllable platelet gel receptacle, and tubing, said tubing fluidly couples said controllable platelet receptacle, said controllable coagulant receptacle, and said controllable platelet gel receptacle, further comprising a plurality of valves coupled in-line with said tubing, said plurality of valves operable to control flow amongst the platelet gel applicator, said controllable platelet receptacle, said controllable coagulant receptacle, and said controllable platelet gel receptacle, wherein said controllable platelet receptacle receives said platelet rich plasma obtained from said patient during a surgical procedure by said blood pheresis system, and controllably delivers platelet rich plasma during the surgical procedure to said controllable platelet gel receptacle, wherein said controllable coagulant receptacle stores a coagulant used to produce platelet gel, and controllably delivers coagulant during the surgical procedure to said controllable platelet gel receptacle, wherein said controllable platelet gel receptacle receives platelet rich plasma from said controllable platelet receptacle, receives coagulant from said controllable coagulant receptacle, and controllably delivers platelet gel comprising platelet rich plasma and coagulant to said platelet gel applicator during the surgical procedure, and wherein said platelet gel applicator receives platelet gel from said controllable platelet gel receptacle, and delivers platelet gel to said selected location of said patient from whom the blood was extracted during the surgical procedure.

9. The system of claim 8, wherein the plurality of valves control a first flow path between said controllable platelet receptacle and said controllable platelet gel receptacle, a second flow path between said controllable coagulant receptacle and said controllable platelet gel receptacle, and a third flow path between said controllable platelet gel receptacle and said platelet gel applicator.

10. The system of claim 8, wherein said platelet gel manufacturer further comprises a controllable flushing receptacle for storing a liquid suitable for flushing said tubing, and controllably flushing said liquid through said tubing in order to help prevent clotting in said tubing.

11. The system of claim 6, wherein said platelet gel manufacturer further comprises a platelet syringe, a coagulant syringe, a platelet gel syringe, a flushing syringe, and tubing, said tubing fluidly couples said platelet syringe, said coagulant syringe, said platelet gel syringe, and said flushing syringe, wherein said flushing syringe stores intravenous saline, and controllably flushes said intravenous saline through said tubing in order to help prevent clotting in said tubing, wherein said platelet syringe receives said platelet rich plasma obtained from said patient by said blood pheresis system, and controllably delivers said platelet rich plasma to said platelet gel syringe, wherein said coagulant syringe stores a coagulant comprising thrombin, and controllably delivers said coagulant to said platelet gel syringe, said platelet gel syringe receives said platelet rich plasma from said platelet syringe, receives said coagulant from said coagulant syringe, and controllably delivers a platelet gel comprising said platelet rich plasma and said coagulant to said platelet gel applicator.

12. A platelet gel manufacturer for use with a closed corporeal system for intravenously extracting blood from a patient during a surgical procedure and separating extracted blood to obtain platelet rich plasma, said platelet gel manufacturer comprising a platelet gel applicator, a first platelet syringe, a coagulant syringe, a first platelet gel syringe, and tubing, wherein said tubing fluidly couples said platelet gel applicator, said first platelet syringe, said coagulant syringe, and said first platelet gel syringe, said first platelet syringe receives a first portion of said platelet rich plasma obtained from said patient by said closed corporeal system, and controllably delivers said first portion of said platelet rich plasma to said first platelet gel syringe via said tubing, said coagulant syringe stores a coagulant used to produce platelet gel, and delivers a first portion of said coagulant to said first platelet gel syringe via said tubing, said first platelet gel syringe receives said platelet rich plasma from said first platelet syringe via said tubing, receives said coagulant from said coagulant syringe via said tubing, and controllably delivers a first platelet gel fraction comprising said first portion of said platelet rich plasma and said first portion of said coagulant to said platelet gel applicator via said tubing, and said platelet gel applicator receives platelet gel from said first platelet gel syringe, and delivers said platelet gel to selected locations of said patient during the surgical procedure in order to promote healing at said selected locations, the closed corporeal system and platelet gel applicator comprising a closed loop system.

13. A platelet gel manufacturer of claim 12, further comprising a second platelet gel syringe, wherein said tubing further fluidly couples said second platelet gel syringe with said platelet gel applicator and said coagulant syringe, said first platelet syringe receives a second portion of said platelet rich plasma obtained from said patient by said closed corporeal system, and controllably delivers said second portion of said platelet rich plasma to said second platelet gel syringe via said tubing, said coagulant syringe further delivers a second portion of said coagulant to said second platelet gel syringe via said tubing, said second platelet gel syringe receives said second portion of said platelet rich plasma from said first platelet syringe via said tubing, receive said second portion of said coagulant from said coagulant syringe via said tubing, and controllably delivers a second platelet gel fraction comprising said second portion of said platelet rich plasma and said second portion of said coagulant to said platelet gel applicator via said tubing, and said platelet gel applicator is receives said second platelet gel from said second platelet gel syringe, and delivers said second platelet gel to said selected locations of said patient.

14. A platelet gel manufacturer of claim 13, further comprising a plurality of valves for controlling flow from said first platelet syringe to said first platelet gel syringe and said second platelet gel syringe.

15. A platelet gel manufacturer of claim 12, further comprising a second platelet syringe, a second platelet gel syringe, and a plurality of valves, wherein said tubing further fluidly couples said second platelet syringe and said second platelet gel syringe with said platelet gel applicator and said coagulant syringe, said second platelet syringe is operable to receive a second portion of said platelet rich plasma, and controllably deliver said second portion of said platelet rich plasma to said second platelet gel syringe via said tubing, said coagulant syringe is further operable to deliver a second portion of said coagulant to said second platelet gel syringe via said tubing, said second platelet gel syringe is operable to receive said second portion of said platelet rich plasma from said second platelet syringe via said tubing, receive said second portion of said coagulant from said coagulant syringe via said tubing, and controllably deliver a second platelet gel comprising said second portion of said platelet rich plasma and said second portion of said coagulant to said platelet gel applicator via said tubing, said plurality of valves is operable to control flow from said coagulant syringe to said first platelet gel syringe and said second platelet gel syringe, and said platelet gel applicator is further operable to receive said second platelet gel from said second platelet gel syringe, and deliver said second platelet gel to said selected locations of said patient.

16. A method for manufacturing a platelet gel comprising:

(1) providing a closed-loop blood treatment device including a closed corporeal system, and a platelet gel manufacturer fluidly coupled to the closed corporeal system, the platelet gel manufacturer including a platelet gel applicator, a controllable platelet receptacle, a controllable coagulant receptacle and a controllable platelet gel receptacle, (2) using the closed corporeal system to extract blood from a patient during a surgical procedure, (3) using the closed corporeal system to extract a plasma rich platelet fraction from the extracted blood, (4) delivering the plasma rich platelet fraction to the controllable platelet receptacle (5) delivering the plasma rich platelet fraction from the controllable platelet receptacle to the controllable platelet gel receptacle, (6) delivering coagulant stored in the coagulant receptacle to the controllable platelet gel receptacle, (7) mixing the coagulant with the plasma rich platelet fraction in the controllable platelet gel receptacle to form a platelet gel, (8) delivering the produced platelet gel from the platelet gel receptacle to the platelet gel applicator, and (9) using the platelet gel applicator to apply the platelet gel to a selected body location of said patient during said surgical procedure, wherein the blood is extracted from the patient, the platelet gel is formed, and the platelet gel is applied to said patient during a single surgical procedure, during which time, the extracted blood, plasma rich fraction and platelet gel do not leave the closed loop of the blood device until they are returned to the same patient during the surgical procedure.

17. The method of claim 16 wherein the steps of providing a second controllable platelet receptacle, delivering a second plasma rich platelet fraction to the second controllable platelet receptacle, and delivering the second plasma rich platelet fraction from the second controllable platelet receptacle to the controllable platelet gel receptacle.

18. The method of claim 17, further comprising the steps of providing a second controllable platelet gel receptacle, wherein the step of delivering the second plasma rich platelet fraction from the second controllable platelet receptacle comprises the step of delivering the second plasma rich platelet fraction to the second controllable platelet gel receptacle.

19. The method of claim 18 further comprising the steps of delivering the coagulant stored in the coagulant receptacle to the second controllable platelet gel receptacle, mixing the coagulant with the second plasma rich platelet fraction in the second controllable platelet gel to form a second platelet gel fraction, delivering the produced second platelet gel fraction to the platelet gel applicator, and using the platelet gel applicator to apply the platelet gel to a selected body location of the patient during said surgical procedure.

* * * * *